United States Patent
Eisenhardt et al.

(10) Patent No.: US 6,428,786 B1
(45) Date of Patent: Aug. 6, 2002

(54) COMPOSITION AND METHOD FOR LACTOSE HYDROLYSIS

(75) Inventors: Peter F. Eisenhardt, Philadelphia, PA (US); Leonard P. Smith, Beesley's Point, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 08/421,825

(22) Filed: Jun. 6, 1995

Related U.S. Application Data

(62) Division of application No. 08/128,625, filed on Sep. 28, 1993, now abandoned.

(51) Int. Cl.$^7$ .............................................. A61K 38/47
(52) U.S. Cl. ................................ 424/94.6; 424/94.61
(58) Field of Search ............................. 424/94.6, 94.61; 435/200

(56) References Cited

U.S. PATENT DOCUMENTS

| | | | |
|---|---|---|---|
| 2,681,858 A | 6/1954 | Stimpson | 99/55 |
| 2,826,503 A | 3/1958 | Roberts et al. | 99/54 |
| 3,592,739 A | 7/1971 | Sternberg | 195/66 |
| 3,629,073 A | 12/1971 | Cayle | 195/62 |
| 3,718,739 A | 2/1973 | Cayle | 424/94 |
| 3,816,259 A | 6/1974 | Collinge et al. | 195/62 |
| 3,919,049 A | 11/1975 | Kiuchi et al. | 195/66 R |
| 4,079,125 A | 3/1978 | Sipos | 424/32 |
| 4,229,539 A | 10/1980 | Miwa et al. | 435/207 |
| 4,435,389 A | 3/1984 | Mutai et al. | 424/181 |
| 4,447,412 A | 5/1984 | Bilton | 424/16 |
| 4,895,801 A | 1/1990 | Kan et al. | 435/101 |
| 4,957,860 A | 9/1990 | Kan et al. | 435/101 |

FOREIGN PATENT DOCUMENTS

| | | |
|---|---|---|
| DE | 2554407 | 12/1974 |
| JP | 5115686 | 7/1974 |

OTHER PUBLICATIONS

Rosado et al., Gastroenterology 87(5): 1072–1082 (1984).*
Barillas et al., Pediatrics 79(5): 766–772 (1987).*
H.S. Merki et al., "Pattern of 24 hour intragastric acidity in active duodenal ulcer disease and in healthy controls," *Gut*, vol. 29, pp. 1583–1587, 1988.
M.S. Medow et al., "β–Galactosidase Tablets in the Treatment of Lactose Intolerance in Pediatrics," Am. Journal of Diseases of Children, vol. 144, pp. 1261–1264, Nov. 1990.
D.M. Simmons, "Characterization of the Precipitates of Poorly Water Soluble Drugs and Determination of the Solubilities in Human Gastro–Intestinal Fluids by Microsopy," *Drug Development and Industrial Pharmacy*, 19(10) pp. 1103–1112, 1993.
L. Johnson, "Gastric Secretion" in *Gastrointestinal Physiology*, 4th ed., Mosby, St. Louis, 1991, pp. 73 and 77–9.
H. Minami et al., "The Physiology and Pathophysiology of Gastric Emptying in Humans," *Gastroenterology*, vol. 86(4), pp. 1592–1610, 1984.
J.P.H. Drenth et al., "Diabetic Gastroparesis, A Critical Reappraisal of New Tretment Strategies," *Drugs*, vol. 44(4), pp. 537–539, 1992.
W. R. Hutson et al., "Influence of Gender and Menopause on Gastric Emptying and Motility," *Gastroenterology*, vol. 96(1), pp. 11–16, 1989.
T. K. Chaudhuri, M.D., et al., "Gastric Emptying in Human Disease States," *The American Journal of Gastroenterology*, vol. 86, No. 5, pp. 533–538, 1991.
V. Gekas et al., "Hydrolysis of Lactose: A Literature Review," *Process Biochem*, Feb. 1985.
K. Diem et al., *Documenta Geigy, Scientific Tables*, 7th Ed. Ciba Geigy Corp., Ardsley, NY, 1974, pp. 647 and 656.

* cited by examiner

Primary Examiner—Jean C. Witz

(57) ABSTRACT

The present invention relates to a composition for the enzymatic hydrolysis of lactose containing two lactase enzymes having distinct pH optima. The composition is suitable for treating or controlling the symptoms of lactose intolerance in humans.

23 Claims, 2 Drawing Sheets

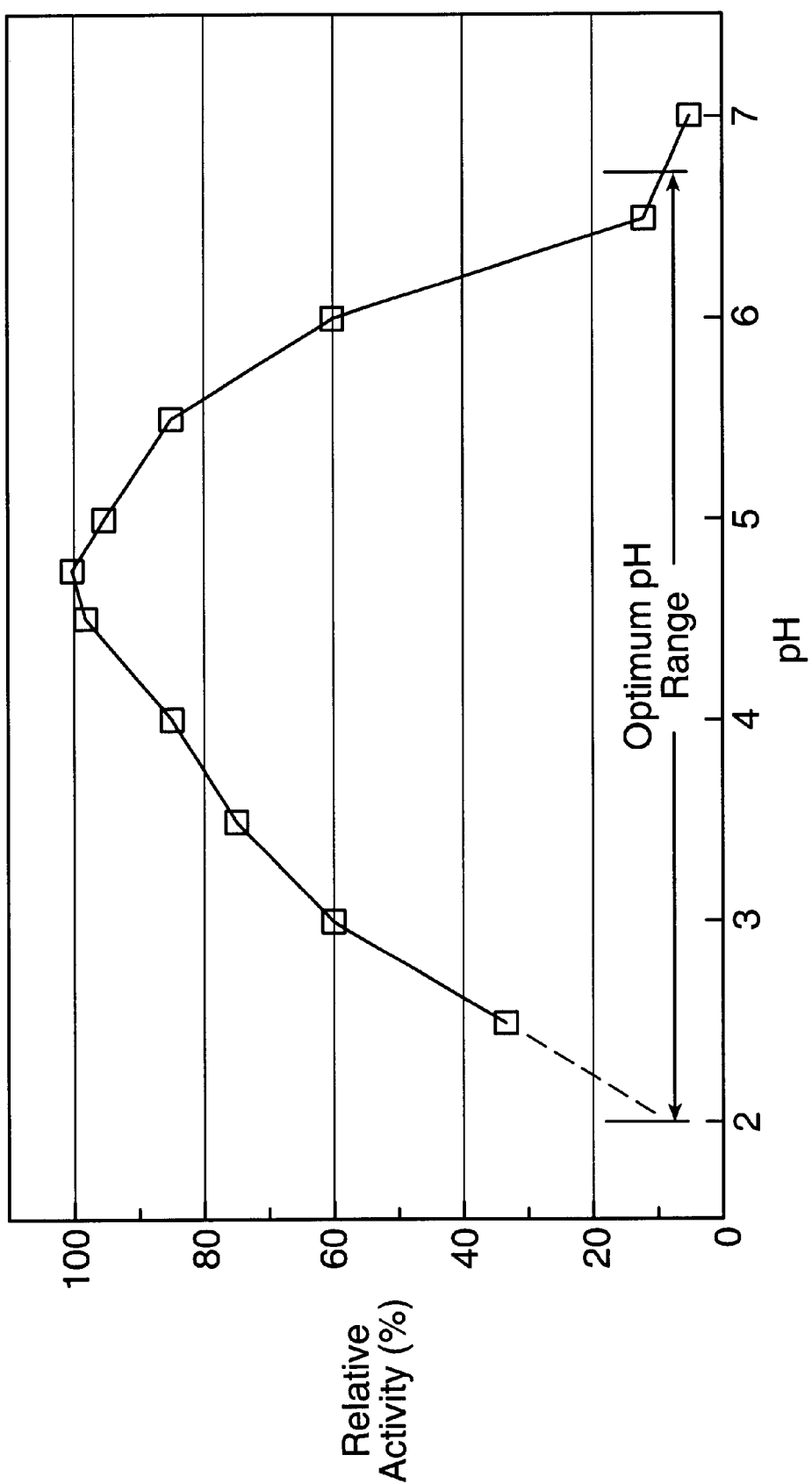

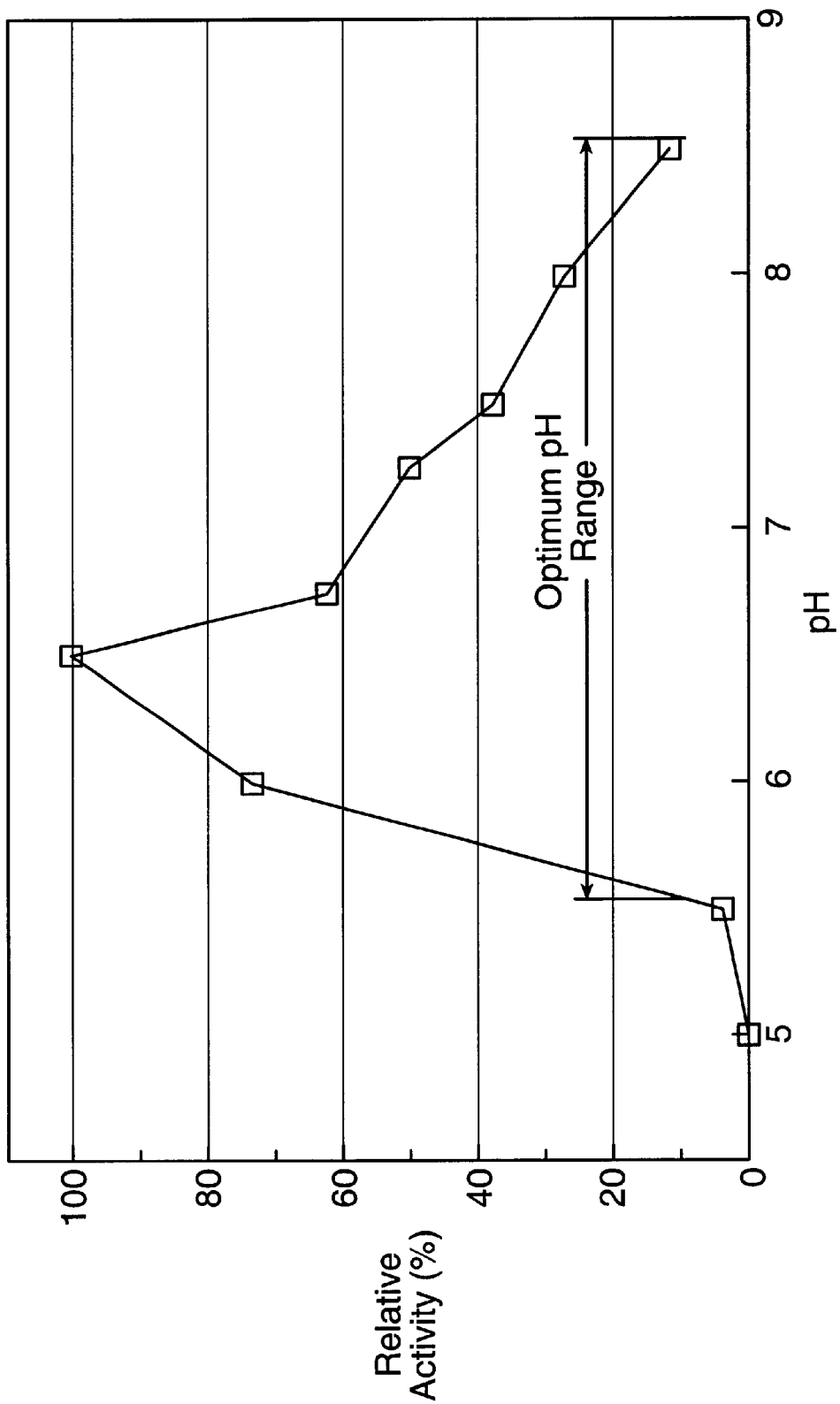

COMPOSITION AND METHOD FOR LACTOSE HYDROLYSIS

This is a division of application Ser. No 08/128,625, filed Sep. 28, 1993, now abandoned, which is hereby incorporated by reference.

FIELD OF THE INVENTION

The present invention relates to a composition and method for the enzymatic hydrolysis of lactose and, more particularly, to treating and controlling the symptoms of lactose intolerance.

BACKGROUND OF THE INVENTION

The human digestive system uses a series of enzymes to break down complex foods into simple molecules that can be absorbed by the body. Milk products contain lactose, which, when hydrolyzed, yield glucose and galactose. This hydrolysis is enzymatically catalyzed by lactase or β-D-galactosidase.

Decreased or non-existent intestinal lactase activity, known as lactose intolerance, is a deficiency that appears in pediatric, adolescent and adult populations. The inability to hydrolyze lactose into its component sugars results in bloating, cramping, abdominal pain, or flatulence after the ingestion of milk or dairy products. In severe cases, malabsorption resulting from lactose intolerance may result in anorexia and weight loss.

Lactose intolerance in humans can be treated in several ways. Prehydrolyzed milk and dairy products, having significantly reduced levels of lactose, are commercially available. Supplements in the form of fungal or yeast-derived lactases that are added to lactose-containing liquids are also available. The lactose may also be in the form of a tablet, which is ingested immediately before the consumption of milk products. Orally administrable tablets containing lactase derived from *Aspergillus oryzae* are available from Lactaid, Inc., Pleasantville, N.J.

A variety of factors influence the effectiveness of lactase-containing tablets in lactose intolerant patients. Tablets containing lactase derived from *Aspergillus oryzae* are intended to hydrolyze lactose in the acidic environment of the stomach. The empty stomach of a healthy human has a pH of 3 or less, but upon the ingestion of food, rises to about 5 or 6. Merki, H. S. et al., "Pattern of 24 Hour Intragastric Acidity in Active Duodenal Ulcer Disease and in Healthy Controls", *Gut*, 29, pp. 1583–87 (1988). Lactases derived from *Asperaillus oryzae* have an optimum pH of approximately 5, and are therefore suitable for the hydrolysis of lactose in the stomach environment. Gekas, V. et al., "Hydrolysis of Lactose: A Literature Review", *Process Biochem*, 20(1), pp. 2–12 (1985).

If a tablet containing lactase derived from *Aspergillus oryzae* is ingested too far in advance of the consumption of lactose-containing food, the lactase may be passed into the more neutral environment of the intestines, having a pH between about 6 and 8. Since the acid-active lactase is relatively inactive in this environment, the lactose may not be enzymatically hydrolyzed, and the symptoms of lactose intolerance may appear. Even if the lactase-containing tablet is ingested at the optimum time before a meal, if a sufficiently large amount of lactose-containing food products is consumed, some undigested lactose may pass to the intestines, resulting in discomfort in the lactose-intolerant patient.

Advances in medicine have increased the life expectancy of the Western world population. The elderly tend to have more neutral stomach pH due to the increase incidence of achlorhydria. There is also an increase in the use of $H_2$ blockers, which results in a more neutral stomach pH. As a result of these trends, the pH profile of the stomach environment for a significant portion of the population is moving out of the optimal range for enzymes derived from *Aspergillus oryzae*.

A need, therefore, exists for a composition which in addition to hydrolyzing lactose under the normal acidic conditions found in a healthy stomach, has enzymatic activity in the more neutral environment of the intestines and in the stomachs of the elderly and users of $H_2$ blockers.

SUMMARY OF THE INVENTION

The present invention provides a composition for the enzymatic hydrolysis of lactose. This composition contains a first, active lactase having a first optimum pH range and a second, active lactase having a second optimum pH range. The first and second optimum pH ranges are of a different magnitude, which enables the composition to enzymatically hydrolyze lactose in environments having different or varying pHs. In a preferred embodiment, the first optimum pH range is about pH 3.0 to about pH 6.0, while the second optimum pH range is about pH 6.0 to about pH 8.0. A process for enzymatically hydrolyzing lactose using the first and second active lactases is also included in the present invention.

In a further embodiment of the present invention, a composition for treating or controlling the symptoms of lactose intolerance is provided. This composition contains a first lactase having an optimum pH range corresponding to the pH of the stomach environment and a second lactase having an optimum pH range corresponding to the pH of the intestinal environment. The composition may further contain a pharmaceutically acceptable, orally administrable carrier material. A method for treating or controlling the symptoms of lactose intolerance using the aforementioned composition is also disclosed.

The compositions and methods of the present invention provide for the enzymatic hydrolysis of lactose under the acidic conditions found in a healthy, human stomach as well as in the more neutral conditions of the intestines and stomachs of $H_2$ blocker users and the elderly suffering from achlorhydria.

BRIEF DESCRIPTION OF THE DRAWINGS

FIG. 1 is plot of hydrolytic activity versus pH for lactase derived from *Aspergillus oryzae*; and FIG. 2 is a plot of hydrolytic activity versus pH for lactase derived from *K. lactis*.

DETAILED DESCRIPTION OF THE PREFERRED EMBODIMENTS

The present invention is characterized by the use of first and second, active lactases, having different optimum pH ranges, for the enzymatic hydrolysis of lactose. This composition may be used to treat or control the symptoms of lactose intolerance in animals, particularly mammals such as humans.

As used in the present invention, "optimum pH range" means the pH over which the hydrolytic activity of the lactase is within about 10 to 100 percent of its maximum, and "optimum pH value" means the pH at which the lactase exhibits maximum hydrolytic activity. FIGS. 1 and 2 show the optimum pH ranges and values for lactase derived from A. oryzae and K. lactis, respectively. The reaction conditions for FIG. 1 were 2.0 $\mu$/mL (micrograms/milliliter) A. oryzae lactase, 4.7% lactose, 30° C. and 10 min. reaction. The reaction conditions for FIG. 2 were 200 $\mu$/mL K. lactis lactase, 0.25% o-nitrophenyl-$\beta$-D-galactoside (substrate), phosphate buffer, 0.1 mM $Mg^{++}$, 37° C. and 15 min. reaction.

The first, active lactase is preferably an enzyme that is capable of catalyzing the hydrolysis of lactose in the stomach. Lactases derived from fungi are generally known to have optimum pH values which fall within the acid range. Gekas, et al., supra, p. 3. The first, active lactase preferably has optimum pH range that encompasses pH 3.0 to about pH 6.0.

The first, active lactase can be derived from the following genera of fungi: Aspergillus; Mucor; Fusarium; Scopuloriopsis; Alternaria; and Curvularia and the bacterium *Thermus aquaticus*. The lactases, having the optimum pH value shown in the parentheses, are preferably derived from the following fungi: *Aspergillus oryzae*; (4.5–5.0) *Aspergillus niger* (3.0–4.0); *Fusarium moniliforme* (3.8–5.0); Scopulariopsis (3.6–5.0); *Mucor pucillus* (4.5–6), *Alternaria alternara* (4.5–5.3); and *Curvularia inaegualis* (3.4–4.3) and the bacterium *Thermus aquaticus* (4.5–5.5).

The second, active lactase has an optimum pH value which falls within the more neutral region. This lactase is capable of catalyzing lactose hydrolysis in the neutral environments of the intestines and the stomachs of the elderly, suffering from achlorhydria, and users of $H_2$ blockers. The optimum pH range for these enzymes preferably encompasses about pH 6.0 to about pH 8.0. Because of this activity in the neutral region, the second, active lactase is capable of hydrolyzing any undigested lactose which may be passed to the intestines, as well as any lactose in the stomach of a user having a more neutral stomach pH.

Lactases derived from yeast and bacteria are generally known to have optimum pH values in the more neutral region (6–7 and 6.5–7.5, respectively). Gekas, et al., supra, p. 2. The second, active lactase can be derived from organisms within the genera of Kluyveromyces (Saccharomyces), Lactobacillus, Bacillus, Streptococcus, and Escherichia. Lactase derived from the following organisms, having the optimum pH value shown in the parentheses, are preferred: *Kluyveromyces lactis* (6.5), *Kluyveromyces fragilis* (6.6), *Lactobacillus thermophilus* (6.2–7.1), *Bacillus circulans* (6.0), *Lactobacillus bulgaricus* (7.0), *Leuconostoc citrovorum* (56.5), *Bacillus stearothermophilus* (6.0–6.4), *Streptococcus thermophilus* (6.5–7.5), and Bacillus sp. (6.8).

In view of the above-noted article by Genkas, et al., which is hereby incorporated by reference, it will be appreciated that the lactases used in the present invention can be produced by a variety of well known techniques. Many of these lactases are produced by commercial processes which cultivate the bacterium, yeast or fungus, and then isolate the lactase from the culture or culture broth of the microorganism. Further techniques for preparing such lactases may be found in U.S. Pat. No. 3,629,073, issued Dec. 21, 1971; U.S. Pat No. 3,718,739, issued Feb. 27, 1973; and U.S. Pat. No. 3,919,049, issued Nov. 11, 1975, all of which are hereby incorporated by reference.

In accordance with another embodiment of the present invention, the second lactase having an optimum pH range encompassing the neutral region nay contain an enteric coating. This coating remains intact in the stomach, but will dissolve and release the second active lactase once it reaches the more neutral environment of the small intestine. The enteric coating protects against irreversal deactivation of the lactase in the stomach, thus making the enzyme available for hydrolysis of lactose in the intestines. However, if the patient suffers from achlorhydria, the second active lactase is generally not enterically coated.

Suitable enteric coatings for the second active lactase include amylose acetate phthalates, styrene-maleic acid copolymer, cellulose acetate succinate, cellulose acetate phthalate, polyvinyl acetate phthalate, hydroxypropylmethylcellulose phthalate, fatty acids, fatty acid esters, glycerol esters, polyglycerol esters, paraffin waxes, carnauba wax, formalized gelatin, shellac and hydrogenated vegetable waxes, such as hydrogenated castor oil and cottonseed oil. Other suitable entric coatings are disclosed in Liebernan, H. A. et al., *Pharmaceutical Dosage Forms: Tablets*, Vol. 3, pp. 114–116 (1990), which is hereby incorporated by reference.

The enteric coating is applied to the second lactase using conventional particle coating techniques. If the second lactase is granulated with other excipients, the resulting granule may also be coated with the enteric material. The enterically coated second lactase will generally contain from about 2 to about 15 weight percent of the enteric coating.

If the composition is intended for use in patients having a more neutral stomach pH, a portion or all of the second lactase particles may be free of the enteric coating. If only a portion of this enzyme in the composition is enterically coated, the uncoated enzyme is, upon ingestion, immediately available for hydrolysis of lactose in the stomach, while the enterically coated enzyme is available for lactose hydrolysis in the intestines.

The lactase compositions of the present invention can be combined with a pharmaceutically acceptable carrier and administered orally. The unit dosages of these compositions may be in the form of solid preparations, such as tablets, pills, capsules, caplets, powders, granules and wafers, or liquid preparations, such as suspensions or dispersions in aqueous or non-aqueous vehicles, such as syrups and elixirs.

In preparing solid unit dosage forms, one first and second lactases are mixed with conventional solid fillers or carriers, such as starch, talc, calcium phosphate, calcium sulfate, calcium stearate, magnesium stearate, stearic acid, sorbitol, mannitol, gelatin, natural or synthetic gums, such as carboxymethylcellulose, methylcellulose, alginates, dextrans, acacia gum, karaya gum, locust bean gum, tragacanth and other conventional carriers. Additionally, other excipients such as diluents, binders, lubricants, disintegrants, colors and flavoring agents may be employed.

Suitable liquid forms of the present invention can be prepared by incorporating the lactase in aqueous or non-aqueous dispersions, suspensions, or solutions. Conventional liquid carriers such as glycerol, and edible glycols, edible oils, such as cottonseed oil, soybean oil, corn oil, peanut oil, safflower oil, and other triglyceride oils, and dispersing or suspending agents, such as the aforementioned natural and synthetic gums.

Conventional methods are employed for preparing the solid and liquid forms of the present invention. Suitable techniques are described in *Remington's Pharmaceutical Sciences*, 18th Ed., Chapters 83 and 89 (1990), which is hereby incorporated by reference.

The lactase compositions of the present invention can also be produced in powdered or granular form for direct admixture with food products consumed by subjects suffering from lactose intolerance. For instance, in the case of a lactose intolerant infant, a suitable amount of the lactase composition of the present invention, in a powdered or granular form, can be added directly to the milk or other food consumed by the infant. In the case of an animal, such as a mammal, that normally requires a dietary regime of whey, the lactase composition of the present invention may be added directly to the whey.

The lactases employed in the compositions are present in therapeutically effective amounts to hydrolyze the lactose normally present in the food products consumed by the subject. This amount, of course, will vary within wide limits, depending in part upon the lactase activity of the particular enzyme, the magnitude of the lactose intolerance in the particular subject and the dietary characteristics of the subject. In general, on an oral unit dosage basis for humans, the composition contains the first lactase in an amount equivalent to about 3000 to about 6000 FCC Lac U and the second lactase in an amount equivalent to about 7000 to about 35,000 neutral lactase units. A FCC lactase unit (FCC Lac U) and a neutral lactase unit are defined as that quantity of enzyme that will liberate 1 $\mu$mol of o-nitrophenol from o-nitrophenyl-$\beta$-D-galactoside per minute under the conditions, of the assay described in Food Chemicals Codex, National Academy Press, Wash., D.C., pp. 491–2 (1981), which is hereby incorporated by reference, at pH 4.5 and 6.5, respectively.

When the composition is in the form of a tablet or other solid form, a unit dosage will generally contain from about 1 to about 15 weight percent of the first lactase, from about 8 to about 80 weight percent of the second lactase and from about 20 to about 80 weight percent of a pharmaceutically acceptable carrier.

The lactase composition is administered to the subject prior to or concurrently with the consumption of lactose-containing food products.

The following example illustrates a specific embodiment of the present invention. This invention, however, is not confined to the specific limitations set forth in this example but rather to the scope of the appended claims. Unless otherwise stated, the percentages and ratios given below are by weight.

EXAMPLE

This example provides a formulation for preparing a caplet form of the present Invention containing an enzyme derived from *Aspergillus oryzae* as the first lactase enzyme having activity in the acid region and an enzyme derived from *Kluyveromyces lactis* as the second lactase having activity in the neutral region. Each caplet has a total weight of 770 mg and an adult human would generally consume two or more caplets per dose.

The lactase powder derived from *K. lactis* is coated with the following enteric suspension:

| Inqredients | % by Wt. |
|---|---|
| Cellulose Acetate Phthalate NF (AQUATERIC Powder) | 11.0 |
| Triacetin, USP | 3.9 |
| Polysorbate 80, NF (TWEEN 80) | 0.1 |
| Purified Water | 85.0 |
| | 100.0 |

The enzyme powder is charged into a Wurster fluidized bed coating apparatus and fluidized by a flow of warm air. The enzyme powder attains a product temperature of 28–37° C. The enteric suspension is then sprayed onto the fluidized enzyme particles at a rate of 9 mL/min. until the coated enzyme particles contain approximately 13% by weight of the enteric coating.

The enterically coated enzyme particles are combined with the following ingredients to produce the caplet:

| Ingredients | mg/Caplet | % W/W |
|---|---|---|
| Enterically Coated Lactase (*K. Lactis*) | 517.6 | 75.0 |
| Lactase Powder (*A. oryzae*) | 15.0 | 2.2 |
| Microcrystalline Cellulose, NF | 153.4 | 22.2 |
| Maqnesium Stearate, NF | 4.0 | 0.6 |
| | 690.0 | 100.0 |

The enterically coated lactase al. (*K. lactis*), lactase derived from *A. oryzae* and microcrystalline cellulose are dry blended in a twin shell blender for 20 min. The magnesium stearate is added to the mixture and blended for an additional 5 min. The mixture is then compressed into a caplet on a rotary tablet press.

Various modifications can be made from the above-described embodiments without departing from a the spirit and scope of the present invention.

What is claimed is:

1. A process for the enzymatic hydrolysis of lactose in mammals with a solid, orally administrable composition comprising first and second active lactases, said process comprising:
    hydrolyzing in the stomach environment having a first pH and a first portion of said lactose with the first, active lactase, said first, active lactase having a first optimum pH range which encompasses said first pH; and
    hydrolyzing in the intestinal environment having a second pH a second portion of said lactose with the second, active lactase, said second, active lactase having a second optimum pH range which encompasses said second pH, said first pH and second pH being of a different magnitude.

2. The process of claim 1 wherein said first pH is more acidic than said second pH.

3. The process of claim 2 wherein said first optimum pH is within the pH range of about 3.0 to about 6.0.

4. The process of claim 3 wherein said first, active lactase is a fungal lactase or a bacterial lactase drived from *Thermus aquaticus*.

5. The process of claim 4 wherein said second optimum pH is within the pH range of about 6.0 to about 8.0.

6. The process of claim 5 wherein said second, active lactase is a yeast or bacterial lactase.

7. The process of claim 6 wherein said second, active lactase is enterically coated.

8. A method for treating or controlling the symptoms of lactose intolerance comprising the oral administration of a solid composition comprising a first lactase having an optimum pH range which encompasses the pH of the stomach environment and a second lactase having an optimum pH range which encompasses the pH of the intestinal environment.

9. The method of claim 8 wherein said composition further comprises a pharmaceutically acceptable carrier material.

10. The method of claim 8 wherein said composition is administered prior to or concurrently with the ingestion of lactose-containing food.

11. The method of claim 8 wherein the optimum pH range of said first lactase encompasses the pH range of about 3.0 to about 6.0.

12. The method of claim 11 wherein said first lactase is a fungal lactase or a bacterial lactase derived from *Thermus aquaticus*.

13. The method of claim 12 wherein said first lactase is derived from the genera of fungi selected from the group consisting of Aspergillus, Mucor, Fusarium, Scopulariopsis, Alternaria, and Curvularia.

14. The method of claim 13 wherein said first is derived from a fungi selected from the group consisting of *Aspergillus oryzae, Aspergillus niger, Fusarium moniliforme,* Scopulariopsis, *Mucor pucillus, Alternaria alternara* and *Curvularia inaegualis*.

15. The method of claim 14 wherein said first lactase is derived from a fungi selected from the group consisting of *Aspergillus oryzae, Aspergillus niger* and *Mucor pucillus*.

16. The method of claim 8 wherein the optimum pH of said second lactase encompasses the pH range of about 6.0 to about 8.0.

17. The method of claim 16 wherein said second lactase is a yeast or bacterial lactase.

18. The method of claim 17 wherein said second lactase is derived from the genera selected from the group consisting of Kluyveromyces, Lactobacillus, and Bacillus, Streptococcus.

19. The method of claim 18 wherein said second lactase is derived from *Kluyveromyces lactis, Kluyveromyces fragilis, Lactobacillus thermophilus, Bacillus circulans, Lactobacillus bulgaricus,* Bacillus sp., *Leuconostoc citrovorum, Bacillus stearothermophilus,* and *Streptococcus thermophilus*.

20. The method of claim 19 wherein said second lactase is *Kluyveromyces lactis*.

21. The method of claim 8 wherein said second lactase is enterically coated.

22. The method of claim 8 wherein the composition is in a unit dosage form comprising an amount of said first lactase equivalent to about 3000 to about 6000 FCC Lac U and an amount of said second lactase equivalent to about 7000 to about 35,000 neutral lactase units.

23. A method for treating or controlling the symptoms of lactose intolerance comprising the oral administration prior to or concurrently with the ingestion of lactose-containing food, a solid, orally administrable composition comprising:

an amount of a lactase derived from fungi selected from the group consisting of *Aspergillus oryzae* and *Aspergillus niger* equivalent to about 3000 to about 6000 FCC Lac U;

an amount of an enterically coated lactase derived from *Kluyveromyces lactis* equivalent to about 7000 to about 35,000 neutral lactase units; and a solid pharmaceutically acceptable carrier.

* * * * *